US012677828B2

(12) United States Patent
Tomich et al.

(10) Patent No.: US 12,677,828 B2
(45) Date of Patent: Jul. 14, 2026

(54) LIPID ENCASING AMPHIPATHIC PEPTIDES

(71) Applicant: Kansas State University Research Foundation, Manhattan, KS (US)

(72) Inventors: John M. Tomich, Manhattan, KS (US); Sheila de Mello Barros, Manhattan, KS (US); Susan K. Whitaker, Manhattan, KS (US); Pinakin Sukthankar, Manhattan, KS (US)

(73) Assignee: Kansas State University Research Foundation, Manhattan, KS (US)

(*) Notice: Subject to any disclaimer, the term of this patent is extended or adjusted under 35 U.S.C. 154(b) by 1001 days.

(21) Appl. No.: 17/441,916

(22) PCT Filed: Mar. 20, 2020

(86) PCT No.: PCT/US2020/023891
§ 371 (c)(1),
(2) Date: Sep. 22, 2021

(87) PCT Pub. No.: WO2020/198020
PCT Pub. Date: Oct. 1, 2020

(65) Prior Publication Data
US 2022/0183277 A1     Jun. 16, 2022

Related U.S. Application Data

(60) Provisional application No. 62/822,370, filed on Mar. 22, 2019.

(51) Int. Cl.
| | |
|---|---|
| *A61K 38/08* | (2019.01) |
| *A01N 25/04* | (2006.01) |
| *A01N 25/26* | (2006.01) |
| *A01N 37/02* | (2006.01) |
| *A01N 47/04* | (2006.01) |
| *A01N 47/34* | (2006.01) |
| *A01P 3/00* | (2006.01) |
| *A01P 7/04* | (2006.01) |
| *A61K 9/107* | (2006.01) |
| *A61K 47/42* | (2017.01) |

(52) U.S. Cl.
CPC ............. *A01N 25/04* (2013.01); *A01N 25/26* (2013.01); *A01P 3/00* (2021.08); *A01P 7/04* (2021.08); *A61K 9/107* (2013.01); *A61K 47/42* (2013.01)

(58) Field of Classification Search
CPC ........ A01N 25/04; A01N 25/26; A01N 37/02; A01N 47/04; A01N 47/34; A01P 3/00; A01P 7/04; A61K 2300/00; A61K 38/08; A61K 47/42
See application file for complete search history.

(56) References Cited

U.S. PATENT DOCUMENTS

| | | | |
|---|---|---|---|
| 7,745,570 | B2 | 6/2010 | Tomich et al. |
| 8,883,967 | B2 | 11/2014 | Tomich et al. |
| 2011/0250237 | A1 | 10/2011 | O'Hagan et al. |
| 2011/0275519 | A1 | 11/2011 | Glatter et al. |
| 2017/0232116 | A1 | 8/2017 | Tomich et al. |
| 2017/0245492 | A1 | 8/2017 | Amir et al. |

FOREIGN PATENT DOCUMENTS

| | | |
|---|---|---|
| EP | 2566322 | 12/2013 |
| JP | 2013525475 | 6/2013 |
| KR | 20110002794 | 1/2011 |
| WO | 2011002258 | 1/2011 |
| WO | 2016007664 | 1/2016 |
| WO | 2016073548 | 5/2016 |
| WO | 2019055988 | 3/2019 |

OTHER PUBLICATIONS

Wang et al., "Stabilization of Lyophilized Pharmaceuticals by Process Optimization: Challenges and Opportunities," American Pharmaceutical Review, Oct. 3, 2012, pp. 1-18. (Year: 2012).*
International Search Report and Written Opinion in corresponding PCT/US2020/023891, dated Aug. 6, 2020.
Mo, et al. "Design of 11-Residue Peptides with Unusual Biophysical Properties: Induced Secondary Structure in the Absence of Water", Biophysical J, 2008, 94, pp. 1807-1817.
Gudlur, et al., "Peptide Nanovesicles Formed by the Self-Assembly of Branched Amphiphilic Peptides", PLOS One, 2012, 7(9), 14 pages.
Shen, et al., "Adhesion and Structure Properties of Protein Nanomaterials Containing Hydrophobic and Charged Amino Acids", Journal of Nanoscience and Nanotechnology, 2006, 6(3), pp. 837-844 (abstract attached).
Office Action in corresponding Japanese Patent Application Serial No. 1020100061403, dated Feb. 20, 2024 (English translation attached).
Extended Search Report in corresponding European Patent Application Serial No. 20779784.6, dated Nov. 17, 2022.
Feng Qui (Chen, et al.), "Self-assembling surfactant-like peptide A6K as potential delivery system for hydrophobic drugs", Int J Nanomedicine, 2015, 10, pp. 847-858.
Fatouros, et al., "Lipid-like Self-Assembling Peptide Nanovesicles for Drug Delivery", ACS Appl. Mater. Interfaces, 2014, 6(11), pp. 8184-8189.
Ouboter, "Rational Design of Purely Peptidic Amphiphiles for Drug Delivery Applications", 2011, pp. 1-133 retrieved from: https://edoc.unibas.ch/1360/1/Dissertation_-_de_Bruyn_Ouboter.pdf.
Barros, et al., "A Review of Solute Encapsulating Nanoparticles used as Delivery Systems with Emphasis on Branched Amphipathic Peptide Capsules", Arch Biochem Biophys., 2016, 596, pp. 22-42.

(Continued)

*Primary Examiner* — Julie Ha

(74) *Attorney, Agent, or Firm* — Hovey Williams LLP; Crissa A. Cook

(57) ABSTRACT
Described herein are linear peptides for creation of colloidal particles and micelles for delivery of active agents. The colloidal particles facilitate encapsulation and delivery of hydrophobic and/or poorly water soluble active agents within the particle hydrophobic core. The compositions are suitable for delivery of active agents to plants and animals.

17 Claims, 8 Drawing Sheets

Specification includes a Sequence Listing.

(56)         References Cited

OTHER PUBLICATIONS

Mikhalevich, et al., "Amphiphilic Peptide Self-Assembly: Expansion to Hybrid Materials", Biomacromolecules, 2017, 18(11), pp. 3471-3480.
Examination Report in corresponding Australia Patent Application Serial No. 2020248745, dated Nov. 21, 2025.

* cited by examiner

Peptide concentration (μM)

Soy oil control    Soy oil + Propionic acid    h5V-L + Soy + PA    h5F-L + Soy + PA
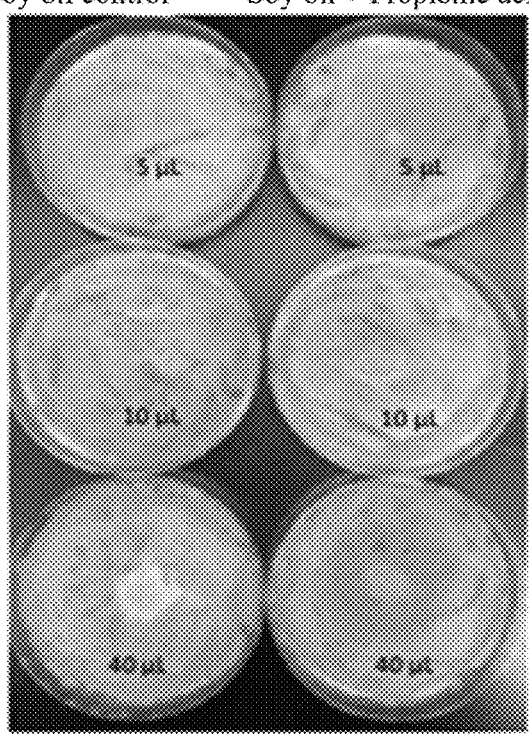
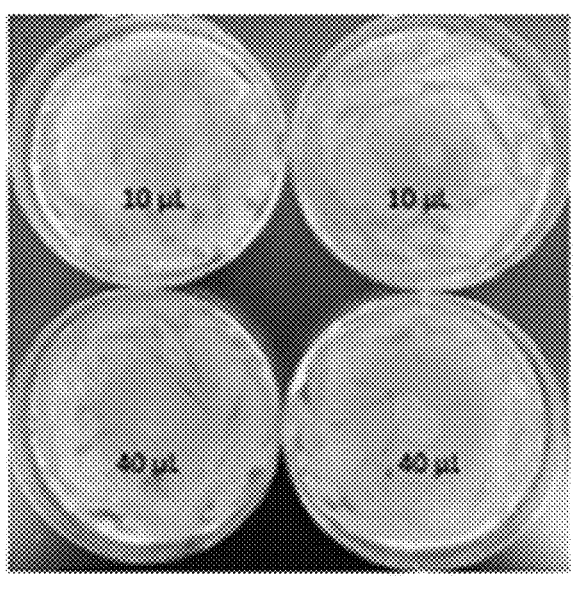
FIG. 5A
FIG. 5B
Soy/PA/Captan    h5V-L +    h5F-L +
                 Soy/PA/Captan    Soy/PA/Captan
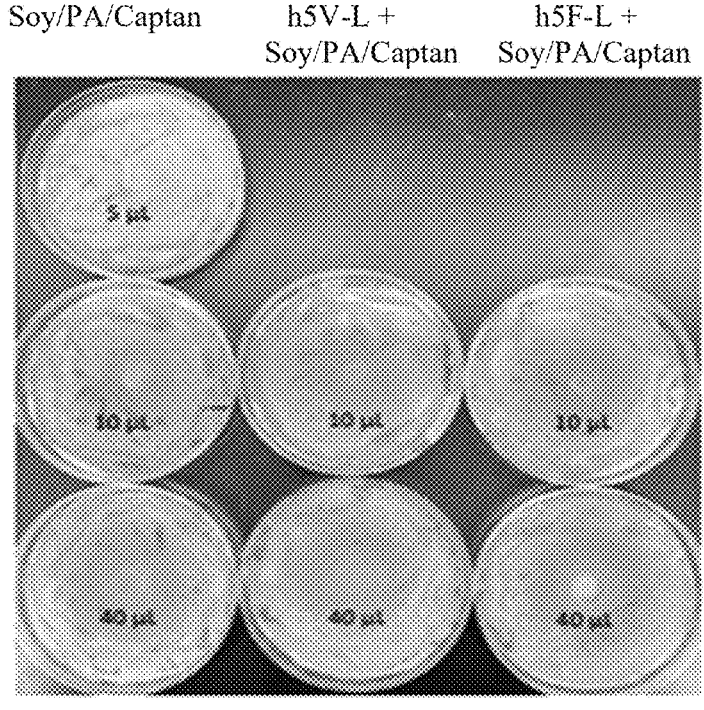
FIG. 5C Soy Oil + Propionic Acid 10 min after foliar application          48 hr after foliar application Soy Oil + Propionic Acid + Captan 10 min after foliar application          48 hr after foliar application Soy Oil + Propionic Acid + Captan + LEAP 10 min after foliar application     48 hr after foliar application

SEQUENCE LISTING

```
<160> NUMBER OF SEQ ID NOS: 3

<210> SEQ ID NO 1
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is F or V

<400> SEQUENCE: 1

Xaa Leu Ile Val Ile Lys Lys Lys Lys Lys
1               5                   10

<210> SEQ ID NO 2
<211> LENGTH: 5
<212> TYPE: PRT
<213> ORGANISM: Artificial Sequence
<220> FEATURE:
<223> OTHER INFORMATION: Synthetic peptide hydrophobic segment
<220> FEATURE:
<221> NAME/KEY: MISC_FEATURE
```

-continued

```
<222> LOCATION: (1)..(1)
<223> OTHER INFORMATION: X is F or V

<400> SEQUENCE: 2

Xaa Leu Ile Val Ile
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic peptide hydrophilic segment

<400> SEQUENCE: 3

Lys Lys Lys Lys Lys
1               5
```

LIPID ENCASING AMPHIPATHIC PEPTIDES

CROSS-REFERENCE TO RELATED APPLICATIONS

The present application is the U.S. National Stage of International Patent Application No. PCT/US2020/023891, filed Mar. 20, 2020, which claims the priority benefit of U.S. Provisional Patent Application Ser. No. 62/822,370, filed Mar. 22, 2019, entitled LIPID ENCASING AMPHIPATHIC PEPTIDES, each of which is incorporated by reference in its entirety herein.

SEQUENCE LISTING

The following application contains a sequence listing in computer readable format (CRF), submitted as a text file in ASCII format entitled "SequenceListing52234-PCT," created on Mar. 18, 2020, as 947 bytes. The content of the CRF is hereby incorporated by reference.

BACKGROUND OF THE INVENTION

Field of the Invention

The present invention relates to peptide-based delivery of active agents, such as via colloidal particles and/or micelles.

Description of Related Art

Conventional approaches for preparing formulations containing hydrophobic active agents have a number of drawbacks, including large structures that agglomerate and eventually lead to complete phase separation. Due to their physical instability and lack of homogeneity, these formulations also suffer from poor and variable absorption. There remains a need for improved technologies for formulating and delivering hydrophobic or poorly soluble active agents.

SUMMARY OF THE INVENTION

The present invention is broadly concerned with compositions comprising a plurality of colloidal particles suspended in an aqueous carrier. The colloidal particles each comprise a peptide matrix with a hydrophobic core and hydrophilic exterior surface. The hydrophobic core advantageously sequesters a non-polar excipient, such as a lipid, oil, or non-polar solvent, optionally along with one or more hydrophobic and/or poorly soluble active agents dispersed or distributed therein.

Also described herein are methods for delivering hydrophobic and/or poorly soluble active agents to a subject in need thereof. The methods comprise administering a composition according to various embodiments described herein to the subject.

The application also concerns methods for delivering hydrophobic and/or poorly soluble active agents to plants. The methods comprise applying a composition according to various embodiments described herein to at least a portion of a plant and/or to the soil where a plant is or will be planted. In some embodiments, the active agents are applied to the plant and/or to the soil where a plant is or will be planted for the purpose of delivery of the active agent to an insect pest.

Also described herein are methods for delivering hydrophobic and/or poorly soluble active agents, specifically insecticides, to insects. The methods comprise contacting the insect with a composition according to various embodiments described herein.

Peptide-based micelles are also described herein, which can encapsulate active agents in their hydrophilic core, and are formed from peptides having the sequence XLIVIK-KKKK (SEQ ID NO:1), where X is F or V.

BRIEF DESCRIPTION OF THE DRAWINGS

FIG. 5A shows an image of control cell culture plates with *A. nidulans* contacted with soy oil only and a soy oil and propionic acid mixture;

FIG. 5B shows an image of cell culture plates with *A. nidulans* contacted with soy oil and propionic acid encased in two different peptide-based colloidal particles;

FIG. 5C shows an image of cell culture plates with *A. nidulans* contacted with the soy oil, propinic acid, and captan mixture alone, and encased in two different peptide-based colloidal particles;

DESCRIPTION

Figure 1:
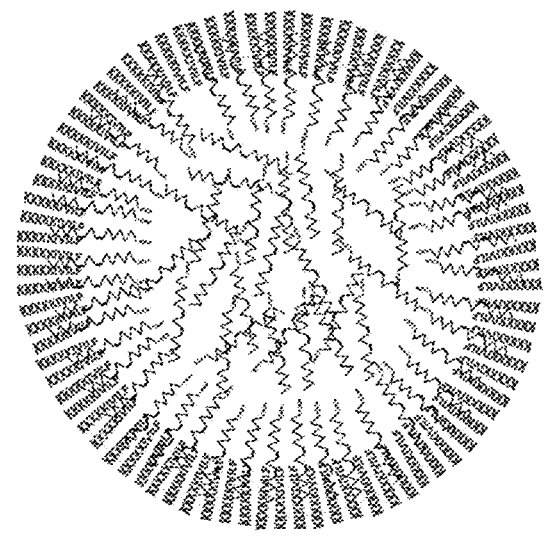
FIG. 1 is an illustration of a peptide-based colloidal particle according to an embodiment of the invention.

Described herein are novel colloidal particles that can be used to encapsulate active agents. In more detail, we disclose the use of linear peptides that are able to encase lipids, oils, and hydrophobic or poorly (water) soluble active ingredients, allowing them to disperse as colloidal particles suspended in an aqueous carrier. Other carriers, adjuvants, synergists, dispersing agents, or solutions may also be included within/with the particles. Advantageously, the outer surfaces of the particles are hydrophilic, allowing them to easily disperse in aqueous solutions, and fostering uptake by animal and plant tissues thereby facilitating the delivery of lipid-soluble active ingredients to the interior of cells. The particles also shield the active agent from the external environment, which could prematurely inactivate the active agent. As drug delivery vehicles, the novel colloidal particles can also be used to alter the biological half-life of an active agent.

The colloidal particles comprise a peptide matrix with a hydrophobic core within which is sequestered a non-polar excipient, such as a lipid, oil, or non-polar solvent, optionally along with one or more active agent agents dispersed or distributed therein. The particle is characterized by a hydrophilic outer surface formed of the hydrophilic segment of the peptides orienting outward towards the external environment in each particle. Preferably, the peptide matrix is homogenous, meaning that it is comprised of a plurality of the same type of peptide (same sequence).

The peptides used to prepare the particles are linear with no branch point, comprising (consisting essentially, or consisting of) a hydrophobic segment (first terminal end) directly connected to a hydrophilic segment (second terminal end). The hydrophobic head groups are preferably each from about 3 residues to about 11 residues in length, and more preferably from about 4 to about 10 residues in length, and even more preferably from about 5 to about 9 residues in length. A preferred hydrophobic sequence is XLIVI ("h5"; SEQ ID NO:2), where X is F or V, preferably F. The hydrophilic (polar) lysine tail sequences are preferably from about 1 to about 7 lysine residues in length, more preferably from about 1 to about 6 lysine residues, and even more preferably from about 1 to about 5 lysine residues. A particularly preferred lysine sequence is KKKKK (SEQ ID NO:3). The peptides preferably have a molecular weight ranging from about 550 Da to about 2300 Da, and more preferably from about 675 Da to about 2050 Da, and even more preferably from about 800 Da to about 1800 Da. The "molecular weight" for these peptides is an average weight calculated based upon the total MW of the actual amino acids present divided by the number of residues. The linear peptides have an overall chain length ranging from 20 amino acid residues or less in length, preferably from about 5 to about 20, more preferably from about 8 to about 15 residues in length, and even more preferably from about 8 to about 12 residues in length. Peptides can be synthesized using traditional Fmoc chemistries.

These peptides are referred to herein as Lipid Encasing Amphipathic Peptides (LEAPs), which include the following preferred sequences: FLIVIKKKKK (SEQ ID NO:1, where X is F) and VLIVIKKKKK (SEQ ID NO:1, where X is V). In one or more embodiments, the peptides comprise an added cysteine residue at the C-terminus of the peptide at the terminal lysine position to facilitate further functionalization. In some embodiments, the N-terminal end of each hydrophobic segment can be capped with an acetyl group (Ac).

In one or more embodiments, functional groups and/or various moieties can be attached to the C-terminal lysine, or the C-terminal carboxyl group, or in the case of a C-terminal cysteine, the free sulfhydryl group. The term "functional moiety" is used herein to encompass functional groups, targeting moieties, and active agents that may be attached to the outer surface of the particle. Exemplary functional moieties that can be attached include fluorophores, dyes, targeting moieties and ligands, antibodies, cysteine, cysteamine, biotin, biocytin, nucleic acids, polyethylene glycol (PEG), organometallic compounds, (e.g., methyl mercury), radioactive labels, conjugating chemistries, —COOH, —CONH$_2$, —SH, and the like. Multiple such moieties can also be attached in a chain of sequential order from the C-terminal end using aliphatic spacers to separate different moieties. Thus, the invention provides the opportunity to create multi-functionalized colloidal particles. Since the individually modified peptides self-assemble to form the matrix, any number of functional moieties at different stoichiometries can be adducted onto individual peptide sequences that comprise part of the assembled colloidal particle.

FIG. 1 provides an illustration of a particle according to an embodiment of the invention. In the figure, the outer shaded layer represents the bulk aqueous carrier that surrounds the colloids. The squiggled lines represent the amphipathic peptides forming the peptide matrix, with their cationic lysine residues facing the aqueous external environment, with the peptides forming a monolayer at the oil-water interface. The hydrophobic amino acids in the sequence point towards the interior/core of the colloid and interact with some of the lipid, oil, or non-polar solvent molecules. The colloidal particles remain stable, as discrete colloidal particles, in an aqueous solution for extended periods of time, without agglomeration, coalescing, or falling apart (preferably for at least 3 months, more preferably at least 6 months, even more preferable at least 12 months). This is referred to herein as the "shelf life" or "shelf stability" of the colloids.

The colloidal particles are prepared by mixing the lipid, oil, or non-polar solvent (excipients) with peptide in a reaction vessel. In one or more embodiments, an active agent is first dispersed or dissolved in the bulk excipient to be encased by the peptides. Preferred lipids and oils are vegetable oils, GRAS vegetable oils, mineral oils, migloyls oils, paraffin oils, Solutol®, and the like, or combinations thereof. The oil may itself be an active in its own right, or it may contain actives. Preferred non-polar solvents include cyclohexane, benzene, n-Decane, piperonyl butoxide, diethyl phthalate, dimethyl sulfoxide and the like, or combinations thereof.

The peptide is added in sufficient quantity to encase all of the excipient present and then allowed to stand for at least about 15 minutes, preferably from about 15 minutes to about 30 minutes. In one or more embodiments, peptide is added at a concentration of from about 0.5 mM to about 5 mM, preferably from about 1 mM to about 3 mM. In one or more embodiments, the weight ratio of peptide to excipient is from about 1:50 to about 1:20, preferably from about 1:25 to about 1:10. Excess distilled/deionized water is then added and mixed using a vortex mixer or bath sonicator for at least about 5 minutes, preferably from about 5 minutes to about 15 minutes. The solution becomes somewhat cloudy as the colloids form and become suspended in the water. Upon centrifugation, the colloids move to the top of the water column, and no more oil layer is visible. As shown in FIG. 1, the hydrophobic amino acids in the peptide sequence point towards the interior of the colloid and interact with the bulk excipient droplet that has been encased.

In one or more embodiments, the resulting colloidal particles have a maximum surface-to-surface dimension of greater than about 100 nm, preferably from about 200 nm to about 1000 nm, more preferably from about 200 to about 800 nm. Advantageously, the particle has a low polydispersity, with a PDI of less than 250%, preferably less than 100%, more preferably less than 50%, more preferably less than 40%, even preferably from about 2% to about 30%. Another important aspect of the design of the colloidal particles is the cationic nature of the solvent-exposed surface. The particles have a zeta potential of from about 1 mV to about 400 mV, preferably from about 20 mV to about 100 mV Advantageously, the colloidal particles can be prepared for targeting of specific cell surface receptors through adduction of the C-terminal lysines with different molecules or functional groups, such as cholesterol, mannose, TAT peptide, insulin, biotin, nucleotides, or any other suitable known surface targeting molecules, and combinations thereof. The colloidal particles having such targeting moieties conjugated to the exterior surface will therefore localize in and be selectively taken up by specific cells or tissues of a patient. Thus, the colloidal particles can be used for targeted therapies (gene therapy, cancer treatment, etc.), and nanodrug delivery by administering the colloidal particles having the targeting moieties to a patient. The targeting moiety is attached to the hydrophilic components of the peptides used to form the colloidal particles, which predominately occupy the outer layer of the particle, thus presenting the targeting moiety on the exterior surface of the colloidal particles after formation. The moiety will be recognized by the targeted region or tissue in the patient, and the colloidal particles will automatically localize in that region or tissue. Targeting these structures to specific cell types could reduce the amount of active ingredient required as well as limit off target effects.

The colloidal particles find application in the cellular deliver of poorly (water) soluble compounds/drugs that are currently too hydrophobic to be delivered effectively. As used herein, references to "poorly soluble" active agents refer to compounds and materials that have low solubility in aqueous solvent systems, and are contrasted with agents that can be fully dispersed or dissolved in aqueous systems. There are numerous synthetic and plant oils that are able to preferentially able to solubilize hydrophobic molecules. The foregoing technology would be useful to prepare, for example, insecticides, fungicides, anti-cancer drugs, and improving the bioavailability of many lipid soluble active ingredients.

The colloidal particles can be used in pharmaceutically-acceptable compositions for delivering the colloidal particles to a subject. In one or more embodiments, the composition comprises a therapeutically-effective amount of colloidal particles dispersed in a pharmaceutically-acceptable carrier. As used herein, a "therapeutically effective" amount refers to the amount of the colloidal particles that will elicit the biological or medical response of a tissue, system, animal, or human that is being sought by a researcher or clinician, and in particular elicit some desired therapeutic effect. One of skill in the art recognizes that an amount may be considered therapeutically effective even if the condition is not totally eradicated but improved partially. As used herein, the term "pharmaceutically-acceptable" means not biologically or otherwise undesirable, in that it can be administered to a subject, cells, or tissue, without excessive toxicity, irritation, or allergic response, and does not cause any undesirable biological effects or interact in a deleterious manner with any of the other segments of the composition in which it is contained. A pharmaceutically-acceptable carrier would naturally be selected to minimize any degradation of the colloidal particles, functional groups, or active gents, and to minimize any adverse side effects in the subject, cells, or tissue, as would be well known to one of skill in the art. Pharmaceutically-acceptable ingredients include those acceptable for veterinary use as well as human pharmaceutical use. Exemplary carriers and excipients include aqueous solutions such as normal (n.) saline (~0.9% NaCl), phosphate buffered saline (PBS), and/or sterile water (DAW), oil-in-water or water-in-oil emulsions, and the like.

Also described herein is a method of targeting delivery of an active agent to a region of a patient comprising administering to a patient, colloidal particles as described herein, which comprises a targeting moiety on the exterior surface. The moiety will be recognized by the targeted region or tissue in the patient, and the colloidal particles will automatically localize in that region or tissue. The colloidal particles can be injected directly into the target tissue, or can be administered systemically.

Also described herein are methods of delivering active agents to plants, such as to the leaves, stems, roots, or other tissues or cells of the plant. The methods can be used to deliver a variety of active agents, including to treat and/or prevent pests, disease, infection, and the like. The method comprises applying the colloidal particles to at least a portion of a plant and/or to the soil where a plant is or will be planted.

Also described herein are methods of delivering active agents to insects by contacting an insect with colloidal particles carrying the active agent, such as an insecticide. The methods can comprise applying the colloidal particles to the leaves, stems, roots, or other tissues or cells of the plant, or otherwise placing the colloidal particles in a location where the insects/pests will come into contact with the colloidal particles. In some embodiments, the colloidal particles may be ingested by the insects. In some embodiments, the colloidal particles can be provided in an insect bait, along with an edible insect attractant (sugars, carbohydrates, yeast, fats, oils, proteins). The bait can be in the form of a liquid, gel, or solid tablet or granules.

An alternative embodiment involves the formation of micelles using the linear peptides. This embodiment involves dispersing the peptides in aqueous solution, upon which they spontaneous assemble into relatively small (i.e., less than about 150 nm) micelles. Over time, the micelles aggregate into larger structures. An active agent could be first dispersed into the aqueous solution for subsequent encapsulating in the micelles for delivery to a patient.

The technology described herein can be used to deliver a wide variety of active agents, including, without limitation, fungicides, anticancer agents, insecticides, herbicides, metabolic inhibitors, etc.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

EXAMPLES

The following examples set forth methods in accordance with the invention. It is to be understood, however, that these examples are provided by way of illustration and nothing therein should be taken as a limitation upon the overall scope of the invention.

Example 1

Peptides were synthesized using Fmoc chemistries. Two different cleavage protocols were tested that yielded two different counter ions: trifluoroacetate ($TFA^-$) and chloride ($Cl^-$). The chloride counterion proved better for this application.

Figure 2:
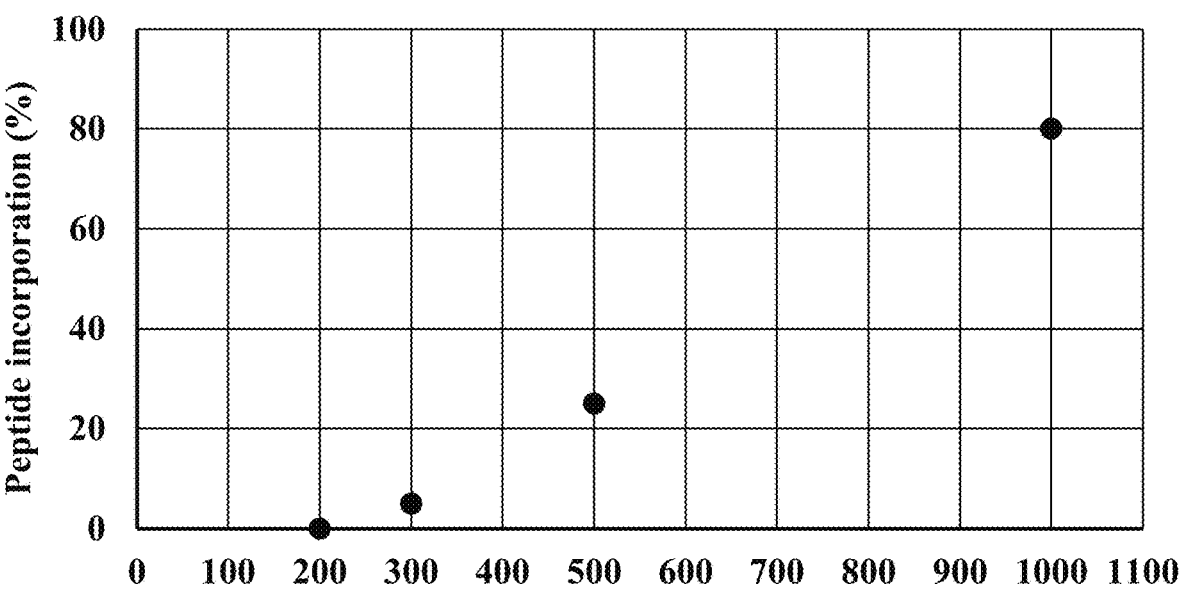
FIG. 2 is a graph of the relationship between peptide concentration and the percentage of peptide incorporated into the colloidal particles when mixed with the non-polar excipient.

Initial encapsulation studies were carried out using high purity soy oil containing a lipid soluble dye, Nile Red. Studies were carried out using FLIVI-KKKKK (SEQ ID NO:1, where X is F). Increasing concentrations of the peptide (see FIG. 2) were prepared in Trifluoroethanol and dried in vacuo. To each tube, 22 µL of soy oil containing Nile Red dye (1 mg/mL) was added and allowed to stand for 15 min. Distilled/deionized water (480 µL) was then added and mixed repeatedly using a vortex mixer over a period of at least 5 min. The solution became somewhat cloudy as the dye containing colloids formed at the higher peptide concentrations. 25% was encapsulated at 0.5 mM peptide concentration with 80% encapsulated by the 1 mM peptide concentration. The colloids formed using the FLIVI-KKKKK (SEQ ID NO:1, where X is F) sequence remain stable in a water solution for extended periods of time (at least 12 months).

Example 2

Peptide colloids were prepared with either Ac-FLIVI-KKKKK-CO-NH$_2$ (SEQ ID NO:1, where X is F, "h$_5$F-L") or Ac-VLIVI-KKKKK-CO-NH$_2$ (SEQ ID NO:1, where X is V, "h$_5$V-L"), in high purity soy oil were tested for average size and zeta potential (surface charge) using light scattering on a ZetaPlus particle sizing instrument. The results for the two peptides are shown in the table below. A control was prepared using high purity soy oil mixed with water and sonicated.

TABLE

| h$_5$F-L |
| --- |
| Elapsed Time 00:02:30 |
| Median Diam. 363.8 nm |
| Mean Diam. 408.4 nm |

TABLE-continued

| Polydispersity 0.260 GSD 1.618 | | |
| --- | --- | --- |
| d(nm) | G(d) | C(d) |
| 164.8 | 26 | 5 |
| 196.3 | 44 | 10 |
| 221.0 | 58 | 15 |
| 242.6 | 70 | 20 |
| 263.0 | 80 | 25 |
| 282.7 | 87 | 30 |
| 302.3 | 93 | 35 |
| 322.1 | 97 | 40 |
| 342.4 | 99 | 45 |
| 363.8 | 100 | 50 |
| 386.5 | 99 | 55 |
| 410.8 | 97 | 60 |
| 437.8 | 93 | 65 |
| 468.1 | 87 | 70 |
| 503.1 | 80 | 75 |
| 545.5 | 70 | 80 |
| 598.8 | 58 | 85 |
| 674.1 | 44 | 90 |
| 802.7 | 26 | 95 |

| h$_5$V-L Elapsed Time 00:02:30 Median Diam. 216.5 nm Mean Diam. 236.8 nm Polydispersity 0.197 GSD 1.528 | | |
| --- | --- | --- |
| d(nm) | G(d) | C(d) |
| 107.8 | 26 | 5 |
| 125.7 | 44 | 10 |
| 139.6 | 58 | 15 |
| 151.5 | 70 | 20 |
| 162.7 | 80 | 25 |
| 173.4 | 87 | 30 |
| 183.9 | 93 | 35 |
| 194.5 | 97 | 40 |
| 205.2 | 99 | 45 |
| 216.5 | 100 | 50 |
| 228.4 | 99 | 55 |
| 241.0 | 97 | 60 |
| 254.8 | 93 | 65 |
| 270.3 | 87 | 70 |
| 288.1 | 80 | 75 |
| 309.3 | 70 | 80 |
| 335.8 | 58 | 85 |
| 372.7 | 44 | 90 |
| 434.7 | 26 | 95 |

The h$_5$F-L peptide yielded a mean diameter of around 410 nm with a polydispersity index (PDI) of 0.23 (upper panel) while the h$_5$V-L peptide (lower panel) gave a smaller mean diameter of around 240 nm with a PDI of 0.2. PDI values of less than 0.3 are considered monodispersed in the pharmaceutical industry. The sizes of the suspended lipid droplets in the control sample were larger than that observed for the peptide colloids, and increased over time as the lipid droplets further coalesced, ultimately separating from the water to form an oil layer on top of the water. The polydispersity index for the control was higher than 0.3.

Regarding zetal potential, the larger h$_5$F-L particle had a value of 46±2.5 mV while the smaller h$_5$V-L particle had a value of 43±1.6 mV. These very positive values are the result of the highly cationic surface of the particles that are imparted by the presence of the oligo-lysine segments that are solvent exposed. These values are also an indicator of the stability of the particles in terms of remaining mono-dispersed. Positive zeta potentials are also associated with efficient cellular uptake of nanoparticles. The values observed for these new colloids are similar to those observed for of patented branched amphipathic peptide capsules that are readily take up by different cell types.

Given that particle sizes for both peptides were above the nanoscale cutoff of 100 nm, the samples were subjected to resizing by extruding them through 100 nm polycarbonate filters. The $h_5F$-L particles were resized to about 80 nm after extrusion (data not shown). The $h_5V$-L particles could be resized to about 90 nm.

Example 3

The ability of LEAPs to deliver a lipid soluble active ingredient to an organism was tested using the antifungal agent Captan: (3aR,7aS)-2-[(Trichloromethyl)sulfanyl]-3a, 4,7,7a-tetrahydro-1H-isoindole-1,3(2H)-dione. This compound is readily soluble in solvents such as acetone and xylene but 4000-fold less in water. The compound also has good solubility in the $C_3$ organic acid, propionic acid. It should be noted that propionic acid by itself has anti-fungal activity. For this experiment two different peptides were tested: $h_5F$-L and $h_5V$-L.

Figure 3:
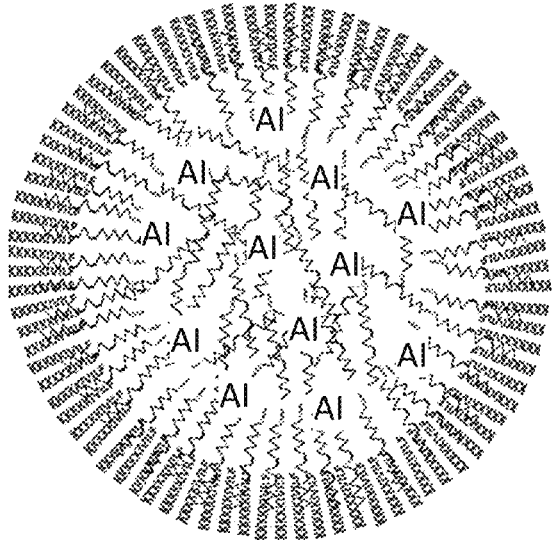
FIG. 3 is an illustration of a peptide-based colloidal particle according to an embodiment of the invention showing an active ingredient (AI) sequestered within the particle with the non-polar excipient.

A 0.5% solution of Captan was prepared in a 1:1 mixture of propionic acid and soy oil (final volume of 10 μL for each peptide). The solution was added to 1 mg of dried peptide. After incubating for 15 min, water (490 μL, pH=3) was added dropwise, then sonicated in a bath sonicator for 5 min at 37° C. and allowed to stand for 20 min. The sample was then centrifuged at room temperature for 10 min at 14K×g. At this point each peptide-lipid complex formed a whitish film on the surface of the water. The volume of water was reduced using a Pipetman leaving a final volume of 150 μL. The solution was again vortexed to resuspend the colloids. An illustration of the colloidal particle with the active ingredient distributed throughout the colloidal body is shown in FIG. 3. A number of different controls were tested along with the peptides prepared with all of the components: soy oil only, soy oil+propionic acid, soy oil+propionic acid+Captan. Volumes of from 5 to 40 μL were spotted on spore seeded plates of *Aspergillus nidulans* grown on 1% skim milk agar gel) yielding 0.33 and 1.33 μg of active agent delivered, respectively (FIG. 4).

Figure 4:
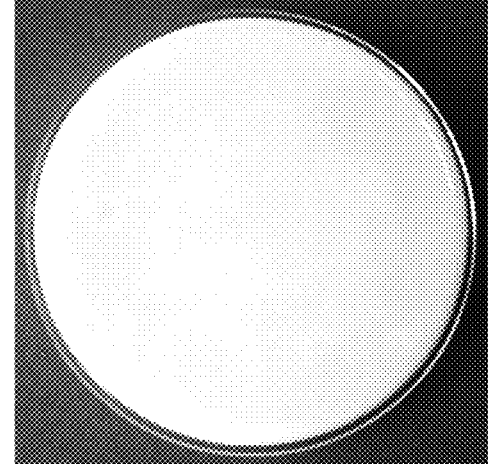
FIG. 4 shows an image of a cell culture plate with *Aspergillus nidulans* grown on 1% skim milk agar gel.

In FIG. 4, lawns of A. were seeded just before testing. The actively growing fungus appears greenish yellow in color. For controls (FIG. 5A) soy oil and soy oil+propionic acid (1:1, v/v) were applied directly to the plates at the indicated volumes. The 40 μL soy oil (FIG. 5A, column 1) shows some antifungal activity however when it is diluted in half in the 1:1 soy plus propionic acid (FIG. 5A, column 2) this effect is greatly diminished. When the 1:1 soy plus propionic acid was separately encased using the two peptides (FIG. 5B, columns 1 and 2) there was minimal antifungal activity. In FIG. 5C, column 1, Captan was dissolved in the propionic acid prior to mixing with the soy oil. The topical application of this mixture was not very effective as an anti-fungal agent. When this mixture was encased in the h5V-L peptide (FIG. 5C, column 2) a small amount of antifungal activity was observed. However, when the mixture was encased in the $h_5F$-L peptide (FIG. 5C, column 3) complete growth inhibition of the fungus was observe as judged by the reappearance of the white milk-agar surface. This result indicates that the Captan is most effective at killing when complexed with oil and internalized by the organism using the LEAP system.

Example 4

Figure 6:
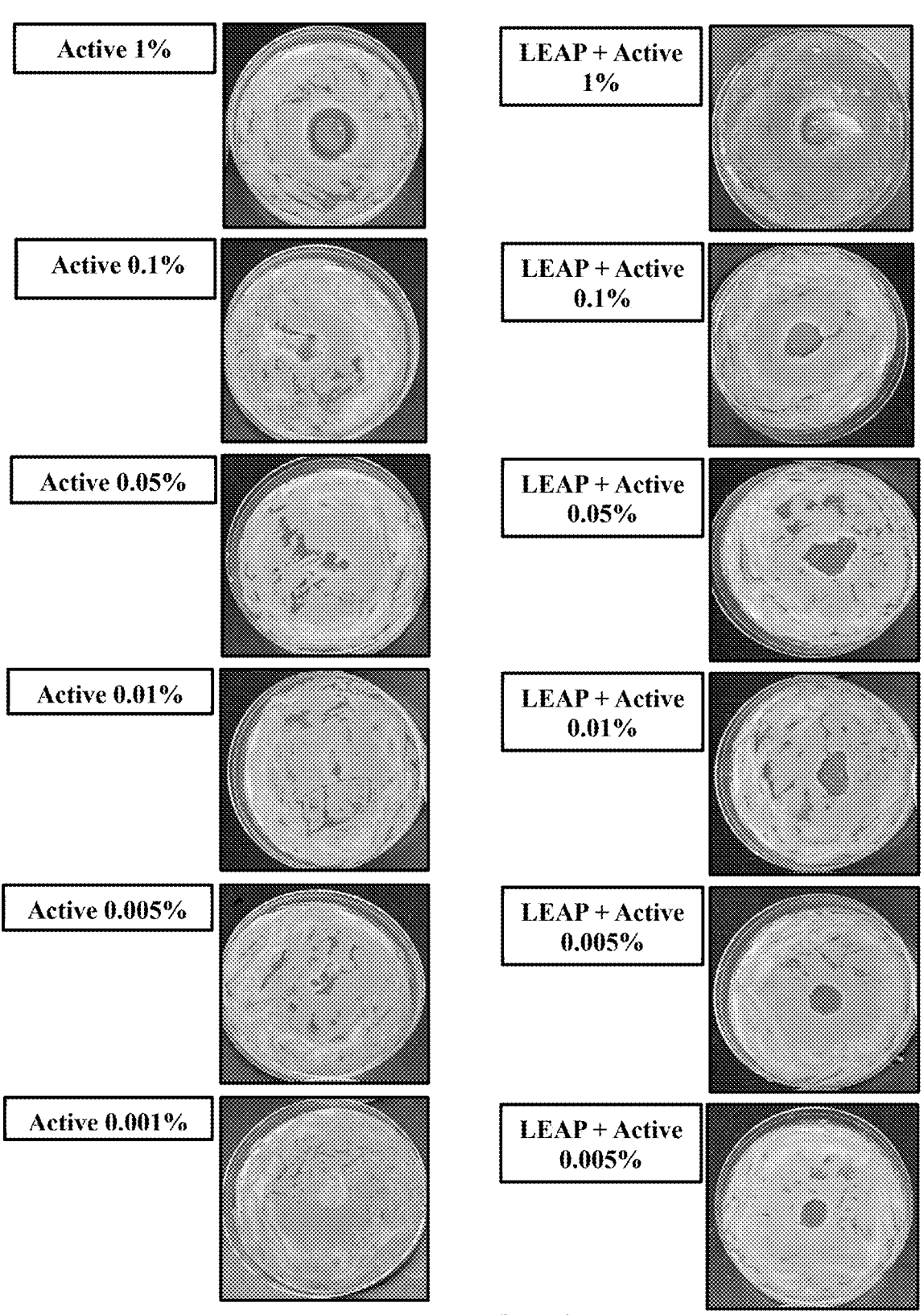
FIG. 6 shows images of cell culture plates with *A. nidulans* comparing the effectiveness of Captan (Active) alone or encased in a LEAP colloidal particle at different concentrations.

In this example, the effectiveness of Captan alone or encased in a LEAP colloidal particle on *A. nidulans* growth was compared. Different concentrations of Captan were tested for growth inhibition when applied directly to freshly seeded fungi growing on 1% milk plates or after encapsulation as a colloidal particle with a LEAP ($h_5F$-L). Captan was dissolved in a formulated (1:1:2) solution containing propionic acid, soy oil, and a pesticide synergist, Piperonyl butoxide (PBO). The resulting active solution was diluted to the following concentrations: 1%, 0.1%, 0.05%, 0.01%, 0.005%, 0.001%. A volume of 50 μL of the 1:1:2 solution containing the fungicide was combined with 1 mmole of dry peptide and then allowed to stand for 20 minutes. Deionized water was then added to the colloidal mixture to raise the total volume to 1 mL, followed by sonicating the mixture for 5 minutes, and then incubating for 60-90 minutes. A volume of 50 μL for each test solution was added to the center of each plate (FIG. 6).

The LEAP colloidal particles containing the actives were significantly more efficient in delivering inhibitory concentrations compared to applying the compound alone. They exhibited near complete growth inhibition, even at the lowest doses of active ingredient. The Captan by itself showed strong growth inhibition only at the highest concentration (left column). There was only slight inhibition observed with the 0.1% concentration. Using LEAPs to prepare colloidal particles containing the active agents showed growth inhibition at all concentrations tested (right column). These results are attributable to to the improved cellular uptake of the LEAP colloidal particles. It will be appreciated that employing this technology could permit growers to use greatly reduced amounts of active ingredients without affecting the effectiveness of the treatment.

Example 5

In this study, we looked at the effects of the Captan fungicide formulation with and without the LEAP peptide when applied to the leaves of Vicia faba (Fava beans). Three formulations were prepared for this experiment:

|  | Soy oil | Proponic acid | Captan | LEAP ($h_5F$-L) |
|---|---|---|---|---|
| 1 | 50 μL | 50 μL | — | — |
| 2 | 50 μL | 50 μL | 5 mg/mL | — |
| 3 | 50 μL | 50 μL | 5 mg/mL | 1 mM final concentraion |
| Control | — | 50 μL in water | — | — |
| Control | 50 μL in water | — | — | — |

Deionized water was added to each formulation to a final volume 1 mL and allowed to stand at room temperature for 60-90 min. These formulations were each used to spray leaves of *V. faba* with effects registered 10 min after spraying the plants and 48 h after treatment.

Figure 7A:
FIG. 7A shows images of the effects of a soy oil and propionic acid mixture applied to foliage after different time points.
Figure 7A:
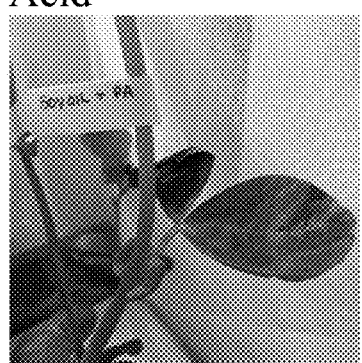
Figure 7B:
FIG. 7B shows images of the effects of a soy oil, propinic acid, and captan mixture applied to foliage after different time points.
Figure 7B:
Figure 7C:
FIG. 7C shows images of the effects of a soy oil, propinic acid, and captan mixture encased in a LEAP colloidal particle applied to foliage after different time points.
Figure 7C:

As expected, the leaves treated with water alone or soy oil in water showed no deleterious effects. However, propionic acid in water caused black spots on the leaves after 24 hr (data not shown). The leaves sprayed with formulations containing soy oil combined to propionic acid also exhibited extreme damage after 24 h with leaf death around 48 h (FIG. 7A). Nearly identical results were observed on leaves treated with the solution containing soy oil, propionic acid, and Captan (FIG. 7B), with leaves showing a visible damage observed as black spots and leaf death around 96 h (not shown). Meanwhile, the same components when encapsulated in colloidal particles via the LEAPs exhibited only healthy leaves (FIG. 7C) with no signs of damage, even after 5 days (not shown).

When formulated solutions requiring propionic acid to dissolve the Captan came in contact with the leaves, it caused visible damage, observed as black spots or in some cases total damage of the leaf. When analyzing each component of the formulation isolated, it was confirmed that propionic acid was the ingredient responsible for the toxic effect on the leaves. Interestingly, when combined in the LEAP formulation though, the damage caused by propionic acid was suppressed, suggesting that the LEAP colloidal particles are able to promote a protective result.

Example 6

In this example, the lethality of an active ingredient alone or encased in the LEAP colloidal particle on *Manduca sexta* (tobacco hornworm) feeding on treated discs of *Nicotiana tabacumi* (tobacco plant) was investigated.

A different lipophilic active ingredient (Novarulon (1-[3-chloro-4-phenyl]-3-urea) was dissolved in a new formulation that could be encased in colloidal particles by the LEAP peptide. Diethyl Phthalate (DEP), 10% DMSO, and Soy oil, 20 μL were mixed with Novarulon and then combined with 2 mg of $h_5$F-L peptide. The mixture was incubated for 15 min, followed by dropwise addition of deionized distilled water (490 μL, pH=5.5), and sonication in a bath sonicator for 5 min at 37° C. The mixture was then allowed to stand for 20 min. Immediately prior to use Tween-80 (polyoxyethylene (80) sorbitan monooleate, 0.05%) as added as a wetting agent.

For the study, 3-cm discs were cut from live plant leaves The discs were washed, dried, and then immersed in the different test solutions and allowed to dry for 60 min. After drying they were placed on 1.5% Agar in six-well polystyrene culture plates. The leaves were divided into five test groups:

| Test Groups | Treatment |
|---|---|
| 1 | Untreated leaves (Water Control) ("UT_WCT") |
| 2 | DEP + 10% DMSO + Soy Oil |
| 3 | DEP + 10% DMSO + Soy Oil) + $h_5$F-L peptide |
| 4 | Novarulon in water 0.02% (0.2 g/L) ("Nov") |
| 5 | DEP + 10% DMSO + Soy Oil + $h_5$F-L peptide + Novarulon (0.02% 0.2 g/L) ("LEAPs&Nov") |

For the initial experiment, 1-day old (first instar) *M. sexta* larvae were place on the treated leaves and observed for 8 days. The insects were exposed to 12 h of light followed by 12 h of dark in an incubator at 26° C. and 85% RH. Each day, the number of dead larvae were counted. In this experiment, there was no statistical difference between the Novarulon in water and the Novarulon encased by the LEAP colloidal particles (data not shown).

Figure 8:
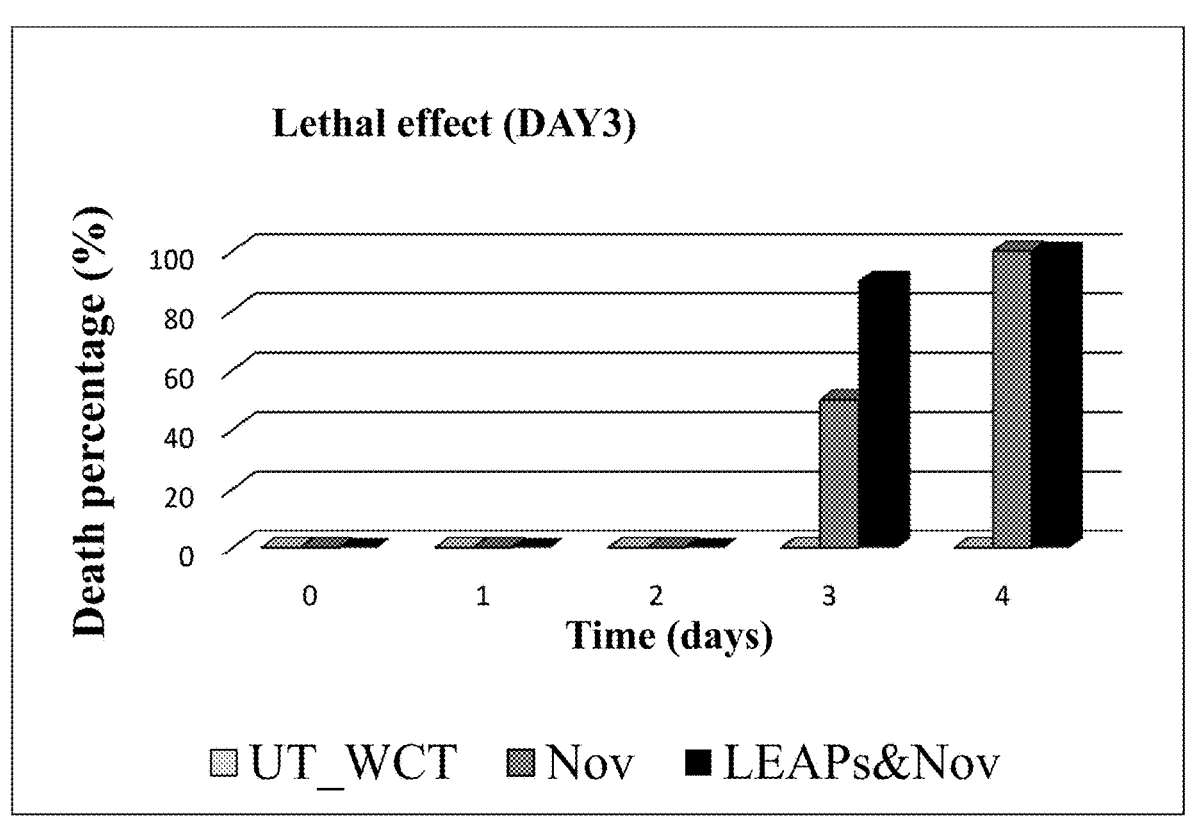
FIG. 8 shows a graph of the effect of different treatments on 1-day old (first instar) *M. sexta* larvae placed on leaves treated with a control ("UT_WCT"), Novarulon alone ("Nov"), or Novarulon encapsulated in a LEAP colloidal particle ("LEAPs&Nov"), after a three day waiting period between treatment and addition of the larvae.
Figure 9:
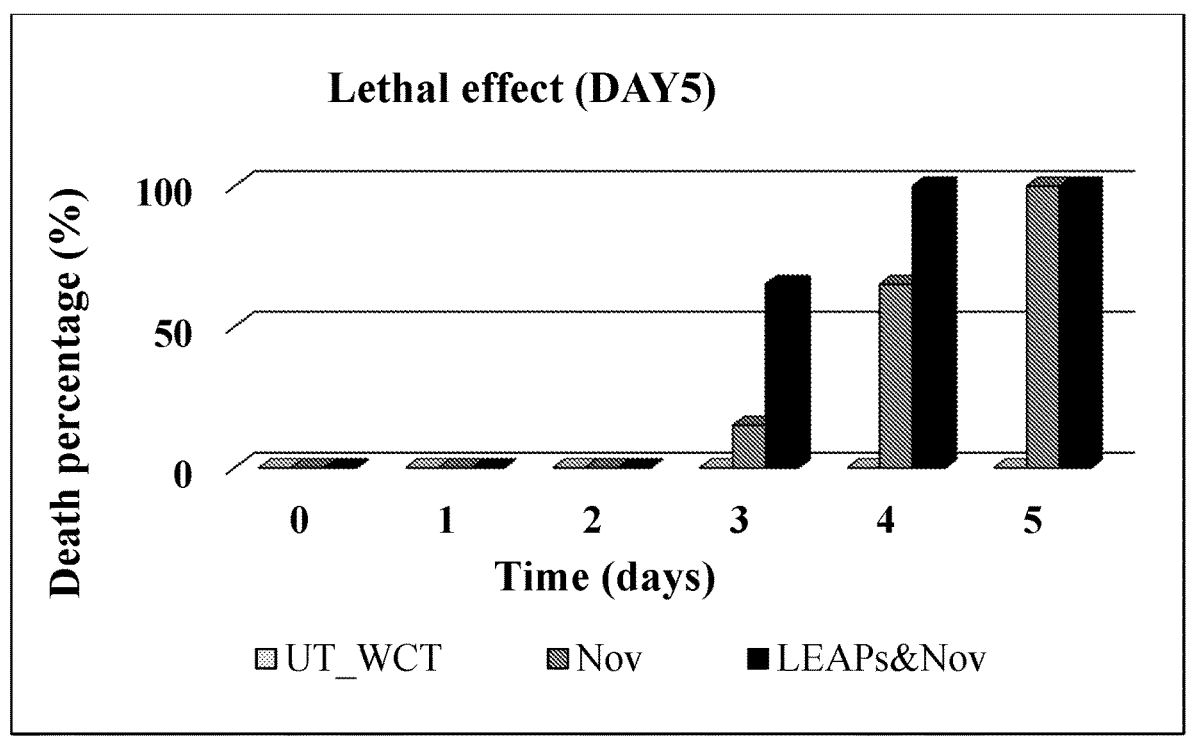
FIG. 9 shows a graph of the effect of different treatments on 1-day old (first instar) *M. sexta* larvae placed on leaves treated with a control ("UT_WCT"), Novarulon alone ("Nov"), or Novarulon encapsulated in a LEAP colloidal particle ("LEAPs&Nov"), after a five day waiting period between treatment and addition of the larvae.

Subsequently, a persistence assay was conducted to see if the LEAP colloidal particles could protect the active ingredient from environmental degradation. Two studies were conducted, one with a 3-day (FIG. 8) and the other with a 5-day (FIG. 9) waiting period before adding the first instar larvae. The methods used to prepare the LEAP colloidal particle encased materials and the preparation of the coated leaves were identical as described above, except that the leaf discs were allowed to sit in the incubator under the previously described conditions outlined above for the designated time period. After the designated waiting period, 1-day old (first instar) *M. sexta* larvae were place on the treated leaves. Each day the number of dead larvae were counted. Examining FIGS. 8 and 9, it is clear to see that the LEAP colloidal particles containing the active ingredient Novarulon started killing faster than the Novarulon control. Under both waiting periods, the LEAP colloidal particles started killing sooner and with higher efficiency. Since the Novarulon by itself was still active it appears that coating the Novarulon containing oil droplet with the peptide appears to have been ingested more efficiently such that the lethal dose was achieved more rapidly.

Example 7

In this study, the ability of the LEAP peptide to encase different non-polar solvents and oils (excipients) was investigated: benzene, cyclohexane, n-decane, mineral oil paraffin (heavy), soy oil and Migloyl® 812N (C8/C10 triglyceride excipient). The non-polar reagents (20 μL) were added to water (480 μL) and sonicated for 15 min. Next, 1 mg of peptide was added to each mixture and sonicated again for an additional 10 min. The samples were then allowed to stand for 24 hr prior to analysis for size, polydispersity by dynamic light scattering, as well as zeta potential. All of these steps were performed at room temperature. The diameters of the particles measured were derived from an assessment of the DLS intensity peak.

TABLE

| Excipient | Diameter (nm) | Polydispersity (%) | Zeta Potential (mV) |
|---|---|---|---|
| Cyclohexane | 220/389 | 30 | 15.9 |
| Benzene | 168 | 27 | 16.6 |
| n-Decane | 804 | 27 | 49.8 |
| Mineral oil paraffin | 687 | 36 | 26.8 |
| Soy oil | 465 | 29 | 44.8 |
| Migloyl ® 812N | 469 | 5.0 | 22.1 |

The results of this study demonstrate that the LEAPs were able to produce stable colloids with positive zeta potentials. The different solvent or oil produced different sized colloids ranging from 169 nm for benzene up to 804 nm for n-decane. Except for cyclohexane, a standard/single colloid size was produced for each of the solvents or oils tested. With the exception of the mineral oil, all of the colloids appear monodispersed with values <30% (0.3 PDI). The presence of a positive zeta potential in a non-polar mixture indicates that the LEAP peptides are oriented in the colloids with the positive oligo-lysyl epsilon amino groups exposed to solvent with their hydrophobic segments oriented towards the core of the colloidal particles.

Being positively charged and monodispersed allows these colloidal structures to be taken up by cells both in vitro and in vivo. It should be noted that the ability of the LEAPs to emulsify and deliver such a variety of non-polar solvents and oils (excipients) to cells, suggests that the platform can be used to deliver a wide variety of hydrophobic active agents that are soluble in this and similar non-polar excipients.

Figure 10:
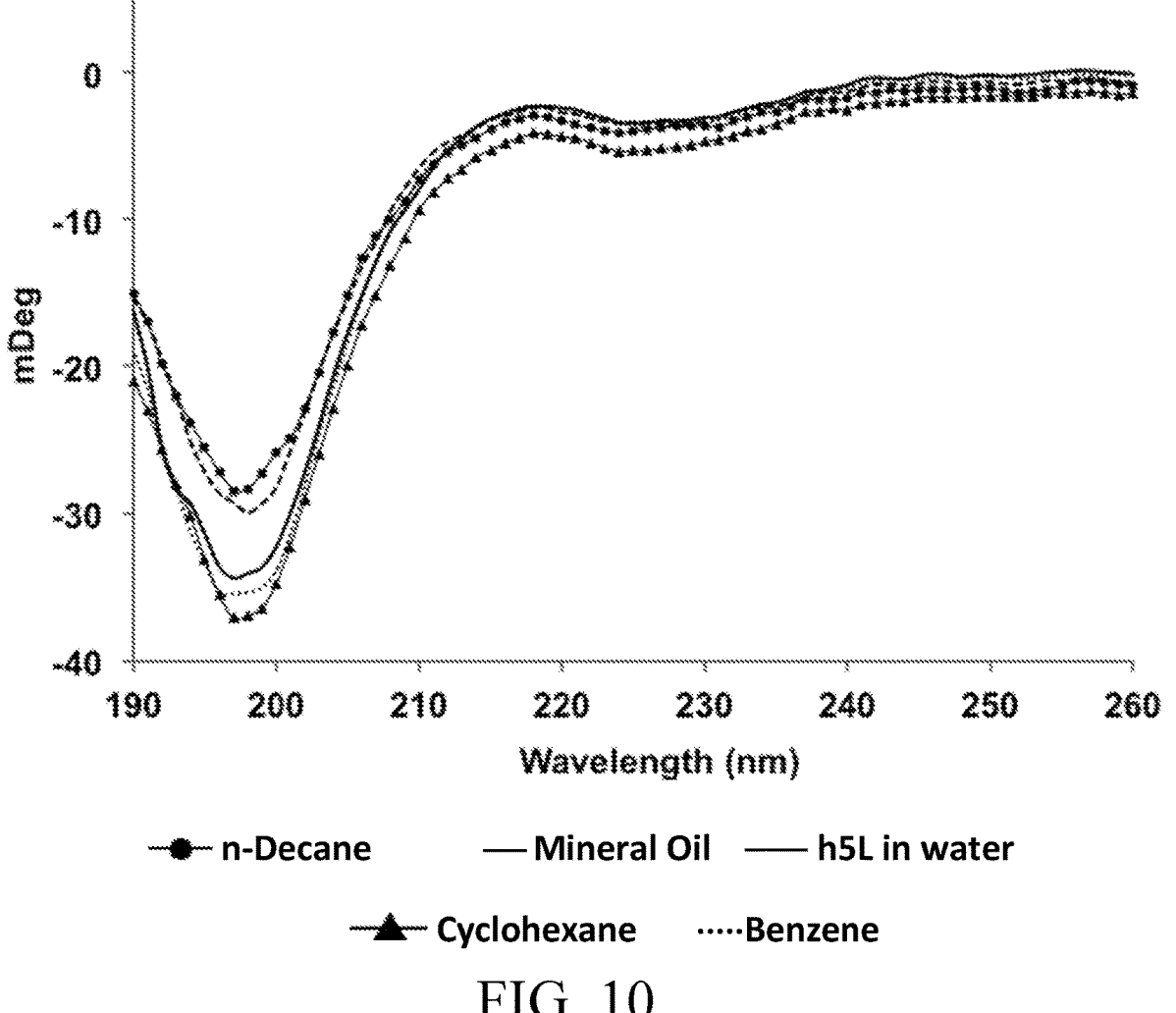
FIG. 10 is a graph of the results from circular dichroism analysis of structures produced from free peptide in water as compared to peptide mixed with various non-polar excipients.

As a second part of this study, the structures of the peptides associated with the non-polar excipients were determined. Circular dichroism was used to analyze the percentages of alpha helix, beta sheet, and random coil in the peptides used to form the colloidal particles. For this analysis only those colloidal solutions that were clear could be used for these measurements (benzene, cyclohexane, n-decane, and mineral oil). Free peptide was included as a control. The results are shown in FIG. 10. The samples were allowed to stand for 5 days before testing. Examining the spectra for these different samples reveals that all of the colloid bound peptides retained the structure of the free peptide indicating that the peptides are not associating with each other to form beta-sheets through the formation of inter-chain hydrogen bonds. Hydrophobic forces appear to be the main stabilizing forces maintaining these structures. These five day old samples were analyzed by dynamic light scattering to show that they were maintaining their 24 hr size and polydispersity values.

Discussion

The initial studies involving colloidal particles with soy oil (SO) investigated the lipid to peptide ratio necessary to encapsulate a lipid soluble dye (Nile red). Since it showed to be efficient when combining approx. 40 to 50 μL of soy oil with 1 mM peptide in a final volume of 1 mL of distilled water, this was the first formulation developed using the LEAP system (FS1). Its first application involving encasing a lipid soluble active ingredient was using the fungicide (Captan) for growth inhibition of *A. nidulans* spores in culture. In order to improve Captan solubility, propionic acid was added to the formulation containing soy oil in a ratio of 1:1 yielding a second formulation (FS2).

Subsequent experiments required a higher concentration of the active ingredient, Captan, a synergist (piperonyl butoxide, PBO) was included in the formulation generating a third formulation (FS3) containing propionic acid, soy oil, and PBO (1:1:2). This formulation has shown to be efficient for LEAP assembly and lipophilic fungicide encapsulation and delivery.

In order to determine any possible effect on the leaves, each component of the formulation was separately tested, showing that propionic acid may cause leaf damage, but that the same effect was suppressed in the presence of the peptide component of the LEAP system.

In further studies the peptides were used to deliver an insecticide, Novarulon. A new base formulation was created to improve the stability of this active ingredients, resulting in an adaptation of a fourth formulation (FS4) containing Diethyl Phthalate, 10% DMSO, and soy oil, combined with 2 mg of peptide. This new formulation was tested for its lethal effect on larvae of *M. sexta* on its commonly affected crop, tobacco plants. This formulation demonstrated favorable colloidal formation, no apparent cytotoxicity, and efficient cell uptake, improving the delivery of components used for biological control of insects without any environmental effect.

These positive results of these studies support the favorable use of the peptides for cellular deliver of hydrophobic compounds/drugs that are currently too hydrophobic to be delivered effectively. The LEAP system shows that it can be reformulated to be compatible with two different hydrophobic active ingredients, and in various non-polar excipients. Also having the easily adducted lysines groups in the aqueous phase allows for the addition of various cell/tissue targeting moieties. This could be accomplished by adding a cysteine residue to the terminal lysine residue of the peptide in order to attach other chemical moieties via the free sulfhydryl group. Targeting these structures to specific cell types could reduce the amount of active ingredient required as well as limit off target effects.

Example 8

One mg of the LEAP (Ac-FLIVIKKKK-CONH2, SEQ ID NO:1, where X is F) was dissolved in 500 μL of DDI-RO water. The solution was sonicated for 10 min then allowed to rest at room temperature for approximately 60 min. This solution was further diluted to 10 mL with DDI-RO water prior to dynamic light scattering analysis. Light scattering data was recorded using an Anton-Parr Litesizer 500 instrument and processed using the proprietary 'Kalliope' analysis software. The DLS calculations indicated particles with a hydrodynamic diameter of 928.3 nm with peak numerical intensity at 120.09 nm and a polydispersity index of 229.1%. This data indicates that the peptides will self-associate to form relatively small micelles on average; however, the polydispersity index reveals that they are likely to aggregate leading to many different sized assemblies.

---

The invention claimed is:

1. A composition comprising a plurality of colloidal particles suspended in an aqueous carrier, said colloidal particles each comprising a peptide matrix with a hydrophobic core and hydrophilic exterior surface, wherein the peptide matrix comprises a plurality of linear peptides forming a peptide monolayer, each peptide having a first terminal end and a second terminal end and comprising a hydrophobic segment at the first terminal end directly connected to a hydrophilic segment at the second terminal end, said hydrophilic segment comprising 1 to 7 lysine residues, wherein said peptide monolayer comprises said plurality of linear peptides arranged such that said hydrophilic segments orient outward in each particle to form said hydrophilic exterior surface, and said hydrophobic segments point towards the hydrophobic core, said hydrophobic core sequestering a non-polar lipid, oil, or non-polar solvent, optionally along with one or more hydrophobic and/or poorly soluble active agents dispersed or distributed therein.

2. The composition of claim 1, wherein said hydrophobic segments interact with said non-polar lipid, oil, or non-polar solvent in said hydrophobic core.

3. The composition of claim 1, wherein said hydrophobic segment comprises XLIVI (SEQ ID NO: 2), where X is F or V.

4. The composition of claim 3, wherein the hydrophobic segment is capped with an acetyl group at the N-terminus.

5. The composition of claim 1, wherein said hydrophilic segment comprises KKKKK (SEQ ID NO:3).

6. The composition of claim 5, further comprising a cysteine residue adducted to the C-terminal lysine residue.

7. The composition of claim 1, wherein said peptide is FLIVIKKKKK (SEQ ID NO: 1, where X is F) or VLIVIK-KKKK (SEQ ID NO: 1, where X is V).

8. The composition of claim 1, said exterior surface comprising one or more functional moieties extending therefrom.

9. The composition of claim 1, wherein the peptide matrix is homogenous.

10. The composition of claim 1, wherein said colloidal particles have a maximum surface-to-surface dimension of about 100 nm to about 1000 nm.

11. The composition of claim 1, said composition having a polydispersity index of about 2% to about 30%.

12. The composition of claim 1, said composition having a shelf life of at least 12 months.

13. The composition of claim 1, wherein said active agent is present and selected from the group consisting of fungicides, anticancer agents, insecticides, herbicides, and metabolic inhibitors.

14. A method of delivering hydrophobic and/or poorly soluble active agents to plants, said method comprising applying a composition according to claim 1 to at least a portion of a plant and/or to the soil where a plant is or will be planted.

15. The method of claim 14, wherein said active agent is an insecticide, wherein said composition is applied to at least a portion of a plant and/or to the soil where a plant is or will be planted where it will come into contact with or be ingested by an insect pest.

16. A method of delivering hydrophobic and/or poorly soluble active agents to insects, said method comprising contacting an insect with a composition according to claim 1, said composition comprising an insecticide active agent.

17. The method of claim 16, wherein contacting the insect comprises applying said composition to at least a portion of a plant and/or to the soil where the plant is or will be planted, such that the composition comes into contact with said insect.

* * * * *